(12) United States Patent
Qiu et al.

(10) Patent No.: US 7,666,461 B2
(45) Date of Patent: Feb. 23, 2010

(54) DIFFUSION-CONTROLLABLE COATINGS ON MEDICAL DEVICE

(75) Inventors: Yongxing Qiu, Duluth, GA (US); Fiona Patricia Carney, Atlanta, GA (US); Nichola Kotov, Stillwater, OK (US); John Martin Lally, Lilburn, GA (US); Carol Ann Morris, Duluth, GA (US)

(73) Assignee: Novartis AG, Basel (CH)

(*) Notice: Subject to any disclaimer, the term of this patent is extended or adjusted under 35 U.S.C. 154(b) by 99 days.

(21) Appl. No.: 10/969,280

(22) Filed: Oct. 20, 2004

(65) Prior Publication Data

US 2005/0106207 A1    May 19, 2005

Related U.S. Application Data

(62) Division of application No. 10/153,063, filed on May 22, 2002, now Pat. No. 6,827,966.

(60) Provisional application No. 60/294,397, filed on May 30, 2001, provisional application No. 60/340,806, filed on Dec. 12, 2001, provisional application No. 60/340,410, filed on Dec. 14, 2001.

(51) Int. Cl.
*B05D 3/00* (2006.01)
*G02C 7/04* (2006.01)
*A61F 2/14* (2006.01)

(52) U.S. Cl. ............... 427/2.1; 427/2.14; 427/2.24; 424/422; 424/425; 424/426; 351/159; 351/160 R

(58) Field of Classification Search ............... 427/2.14, 427/2.24, 162, 2.1–2.31; 351/159, 160 R; 424/425, 426, 422
See application file for complete search history.

(56) References Cited

U.S. PATENT DOCUMENTS 4,069,307 A * 1/1978 Higuchi et al. ............... 424/432

(Continued)

FOREIGN PATENT DOCUMENTS

CN    1298707 A * 6/2001

(Continued)

OTHER PUBLICATIONS

Yuri Lvov et al. Molecular film assembly via layer-by-layer adsorption of oppositely charged macromolecules (linear polymer, protein and clay) and concanavalin A and glycogen; Thin Solid Films 284-285 (1996) 797-801.*

(Continued)

*Primary Examiner*—Timothy H Meeks
*Assistant Examiner*—Cachet I Sellman
(74) *Attorney, Agent, or Firm*—Sheng-Hsin Hu; Jian Zhou

(57) ABSTRACT

The present invention provides a method for forming on a medical device, preferably an ophthalmic lens, more preferably a contact lens, a diffusion-controllable coating capable of controlling the out-diffusion or release of guest materials from the medical device. The method of the invention comprises: (1) applying one layer of clay and optionally one or more layers of polyionic materials onto the medical device; or (2) applying alternatively a layer of a first polyionic material and a layer of a second polyionic material having charges opposite of the charges of the first polyionic material onto the medical device and releasing the coated medical device into a releasing medium having a composition capable of imparting a desired permeability to the diffusion-controllable coating on the medical device.

9 Claims, 5 Drawing Sheets

U.S. PATENT DOCUMENTS

| | | | |
|---|---|---|---|
| 4,168,112 A | 9/1979 | Ellis et al. | 351/160 |
| 4,321,261 A | 3/1982 | Ellis et al. | 424/180 |
| 4,652,459 A * | 3/1987 | Engelhardt | 427/2.24 |
| 4,941,997 A | 7/1990 | Decher et al. | 252/586 |
| 4,973,429 A | 11/1990 | Decher et al. | 252/587 |
| 5,068,318 A | 11/1991 | Decher et al. | 534/573 |
| 5,447,724 A * | 9/1995 | Helmus et al. | 424/426 |
| 5,518,767 A | 5/1996 | Rubner et al. | 427/259 |
| 5,529,727 A * | 6/1996 | LaBombard et al. | 264/1.36 |
| 5,536,573 A | 7/1996 | Rubner et al. | 428/378 |
| 5,817,017 A * | 10/1998 | Young et al. | 600/433 |
| 6,011,082 A | 1/2000 | Wang et al. | 523/107 |
| 6,217,896 B1 * | 4/2001 | Benjamin | 424/427 |
| 6,451,871 B1 * | 9/2002 | Winterton et al. | 523/106 |
| 2001/0034500 A1 * | 10/2001 | March | 604/66 |
| 2001/0046564 A1 * | 11/2001 | Kotov | 427/430.1 |

FOREIGN PATENT DOCUMENTS

| | | |
|---|---|---|
| EP | 0 032 443 | 7/1981 |
| EP | 01 138 385 | 4/1985 |
| GB | 2 012 070 | 7/1979 |
| JP | 05318118 | 3/1993 |
| JP | 09230107 A * | 9/1997 |
| WO | WO 95/00618 | 1/1995 |
| WO | WO 95/02251 | 1/1995 |
| WO | WO 95/20407 | 8/1995 |
| WO | WO 96/18498 | 6/1996 |
| WO | WO 96/31792 | 10/1996 |
| WO | WO 96/37241 | 11/1996 |
| WO | WO 00/32838 | 6/2000 |

OTHER PUBLICATIONS

"New Electro-Active Self-Assembled Multilayer Thin Films Based on Alternately Adsorbed Layers of Polyelectrolytes and Functional Dye Molecules", Yoo, Wu, Lee and Rubner, 1997 Elsevier Science S.A., pp. 1425-1426.

"Layer-By-Layer Modification of Surfaces Through The Use of Self-Assembled Monolayers of Polyions", Yoo and Rubner, Supramolecular Science vol. 2 Nubers 3-4, 1995, pp. 2568-2570, pp. 757-758, pp. 169.

"Molecular-Level Processing of Conjugated Polymers. Layer-By-Layer Manipulation of Conjugated Polyions", Ferreira and Rubner, 1995 American Chemical Society, pp. 7107-7114.

"Molecular-Level Processing of Conjugated Polymers. Layer-By-Layer Manipulation of In-Situ Polymerized p-Type Doped Conducting Polymers", Fou and Rubner, 1995 American Chemical Society, pp. 7115-7120.

"Molecular-Level Processing of Conjugated Polymers. Layer-By-Layer Manipulation of Polyaniline via Electrostatic Interactions", Cheung, Stockton and Rubner, Macrmolecules 1997, 30, 2712-2716.

"Blood Compatibility-surface characteristic relationships of a Langmuir-Blodgett film composed of an anionic amphiphile-polycation complex", Uchida, Kunitake and Kajiyama, New Polymeric Mater., vol. 4, No. 3, pp. 199-211 (1994).

"Enhancement of light emitting diodes based on self-assembled heterostructures of poly(p-phenylene vinylene)", Onitisuka, Fou, Ferreira, Hseieh, and Rubner, American Institute of Physics., J. Appl. Phys. 80 (7) Oct. 1, 1996, pp. 4067-4071.

"Investigations of New Self Assembled Multilayer Thin Films Based on Alternately Adsorbed Layers of Polyelectrolytes and Functional Dye Molecules", Yoo, Lee & Rubner, Mat. Res. Soc.Symp. Proc. vol. 413, 1996 Materials Research society, pp. 395-400.

"New Electro-Active Self-Assembled Multilayer Thin Films Based on Alternately Adsorbed Layers of Polyelectrolytes and Functional Dye Molecules", Yoo, Wu, Lee and Rubner, 1997 Elsevier Science S.A., pp. 1425-1426.

* cited by examiner

DIFFUSION-CONTROLLABLE COATINGS ON MEDICAL DEVICE

This application is a division of U.S. patent application Ser. No. 10/153,063 filed May 22, 2002, now U.S. Pat. No. 6,827,966 which claims benefits under 35 U.S.C. §119(e) of U.S. provisional patent application Nos. 60/294,397 filed May 30, 2001, 60/340,806 filed Dec. 12, 2001 and 60/340,410 filed Dec. 14, 2001.

This invention relates to a method for forming a diffusion-controllable coating on a medical device. Such diffusion-controllable coatings may prevent and/or control out-diffusion or out-flow or release of guest materials from a medical device. In addition, this invention relates to a medical device having a diffusion-controllable coating.

BACKGROUND

Ophthalmic lenses have been used for providing an individual with improved visual acuity or visual and/or cosmetic benefits. Recently, it has been proposed that ophthalmic lenses can provide other benefits. For example, ophthalmic lenses can be used as ocular sensors for non-invasive or minimally invasive monitoring of glucose, as disclosed by March in PCT International Publication WO 01/13783. Such ocular sensors for glucose can be used to conveniently, non-invasively and frequently monitor blood glucose levels by determining glucose levels in an ocular fluid, such as tears, aqueous humor, or interstitial fluid, based on the correlation between the blood glucose concentration and the ocular glucose concentration, and whereby to achieve the tight control of blood glucose levels by managing food intake and the dosage and timing of insulin injection. Ocular glucose sensors disclosed by March in PCT International Publication WO 01/13783 can be one potentially useful non-invasive technology.

In order to fully explore the full potential of the ocular glucose sensing technology, there is an issue needed to be addressed. The issue is the out-diffusion of guest materials, such as the fluorescently labeled glucose receptor and/or the fluorescently labeled glucose competitor, from ophthalmic lenses. Such out diffusion may affect the precision and reproducibility of the ocular glucose sensing technology. Therefore, there is a need for a method of forming on an ophthalmic lenses a diffusion-controllable coating capable of controlling out-diffusion or out-flow of guest materials from the ophthalmic lens.

Furthermore, ophthalmic lenses may be served as a device for controlled delivery of therapeutic agents, besides vision corrections. For example, contact lenses may be used as a carrier for drugs to treat eye diseases, e.g., dry eye syndrome. Therefore, there is also a need for a method for forming on an ophthalmic lenses a diffusion-controllable coating capable of controlling release of drugs (guest materials) for treating eye diseases.

In addition, the manufacturing of ophthalmic lenses comprises a lengthy and costly extraction process where unpolymerized materials, such as monomers and macromers in the polymerizable composition for making ophthalmic lenses, are extracted from lenses. It is preferable that such extraction process can be eliminated from the manufacturing of ophthalmic lenses. Therefore, there is a further need for a diffusion-controllable coating capable of preventing unpolymerized raw materials (guest materials) from leaching out of the core of ophthalmic lenses.

One object of this invention is to solve the above problems by using a layer-by-layer coating process to form a diffusion-controllable coating on the surface of medical device, preferably ophthalmic lenses, more preferably contact lenses. Such coating may prevent guest materials from leaching out of the core of ophthalmic lenses or control release of therapeutic agents associated with or entrapped in the medical devices into the eye.

Another object of this invention is to produce medical devices, preferably ophthalmic lenses, more preferably contact lenses, having a diffusion-controllable coating which may prevent guest materials from leaching out of the core of ophthalmic lenses or control release of therapeutic agents associated with or entrapped in the medical devices into the eye.

SUMMARY OF THE INVENTION

This invention is partly based on discoveries that the out-diffusion of guest materials from ophthalmic lenses can be prevented by a diffusion controllable coating on ophthalmic lenses. The diffusion-controllable coating is formed on ophthalmic lenses by using a cost-effective coating process, such as a layer-by-layer (LbL) coating process.

This invention also is partly based on unexpected discoveries that the properties of LbL coating can be manipulated by changing the composition of a releasing and storage medium. Using different releasing and storage media, for example, water or phosphate buffer (PBS), the coating properties (permeability, wettability, thickness, composition, etc.) can be controlled. When using water as releasing and storage medium, LbL coatings on lenses appear to be dense/compact and have lower permeability. When using PBS as releasing and storage medium, LbL coatings on lenses appear to be more loose/fluffy and have higher permeability. Based on contact angle, LbL coatings on lenses are more wettable when using water as releasing and storage medium than when using PBS as releasing and storage medium. It has been also found that the thickness of LbL coatings on silicon wafer may depend upon the composition of a releasing and storage medium. These findings will allow us to tailor coatings with desired properties on any medical device, which will have many applications such as controlled release of different moieties (drug, nutrients, lubricants, etc), and control of out-diffusion of low or high molecular weight moieties, etc.

One aspect of the invention relates to a method for forming on a medical device, preferably an ophthalmic lens, a diffusion-controllable coating capable of controlling the out-diffusion or release of guest materials from the medical device. The method of the invention comprises: (1) applying one layer of clay and optionally one or more layers of polyionic materials onto the medical device; or (2) applying alternatively a layer of a first polyionic material and a layer of a second polyionic material having charges opposite of the charges of the first polyionic material onto the medical device and releasing the coated medical device into a releasing medium having a composition capable of imparting a desired permeability to the diffusion-controllable coating on the medical device.

Another aspect of the invention is a medical device having a diffusion-controllable coating which is capable of controlling the out-diffusion or release of guest materials from the medical device, wherein the diffusion-controllable coating is produced by: (1) applying on the medical device one layer of clay and optionally one or more layers of polyionic materials; or (2) applying alternatively a layer of a first polyionic material and a layer of a second polyionic material having charges opposite of the charges of the first polyionic material onto the medical device and releasing the coated medical device into a releasing medium having a composition capable of imparting a desired permeability to the diffusion-controllable coating on the medical device.

A further aspect of the invention is a method for manufacturing ophthalmic lenses without an extraction process, the method comprising: (1) producing ophthalmic lenses by molding in molds and/or by lathing and (2) forming a diffusion-controllable coating on each of the ophthalmic lenses produced in step (1) by a) applying thereon one layer of clay and optionally one or more layers of polyionic materials, or b) applying alternatively a layer of a first polyionic material and a layer of a second polyionic material having charges opposite of the charges of the first polyionic material onto the medical device and releasing the coated medical device into a releasing medium having a composition capable of imparting a desired permeability to the diffusion-controllable coating on the medical device.

The present invention provides the foregoing and other features, and the advantages of the invention will become further apparent from the following detailed description of the presently preferred embodiments, read in conjunction with the accompanying figures. The detailed description and figures are merely illustrative of the invention and do not limit the scope of the invention, which is defined by the appended claims and equivalents thereof.

DETAILED DESCRIPTION OF THE PREFERRED EMBODIMENTS

Figure 1:
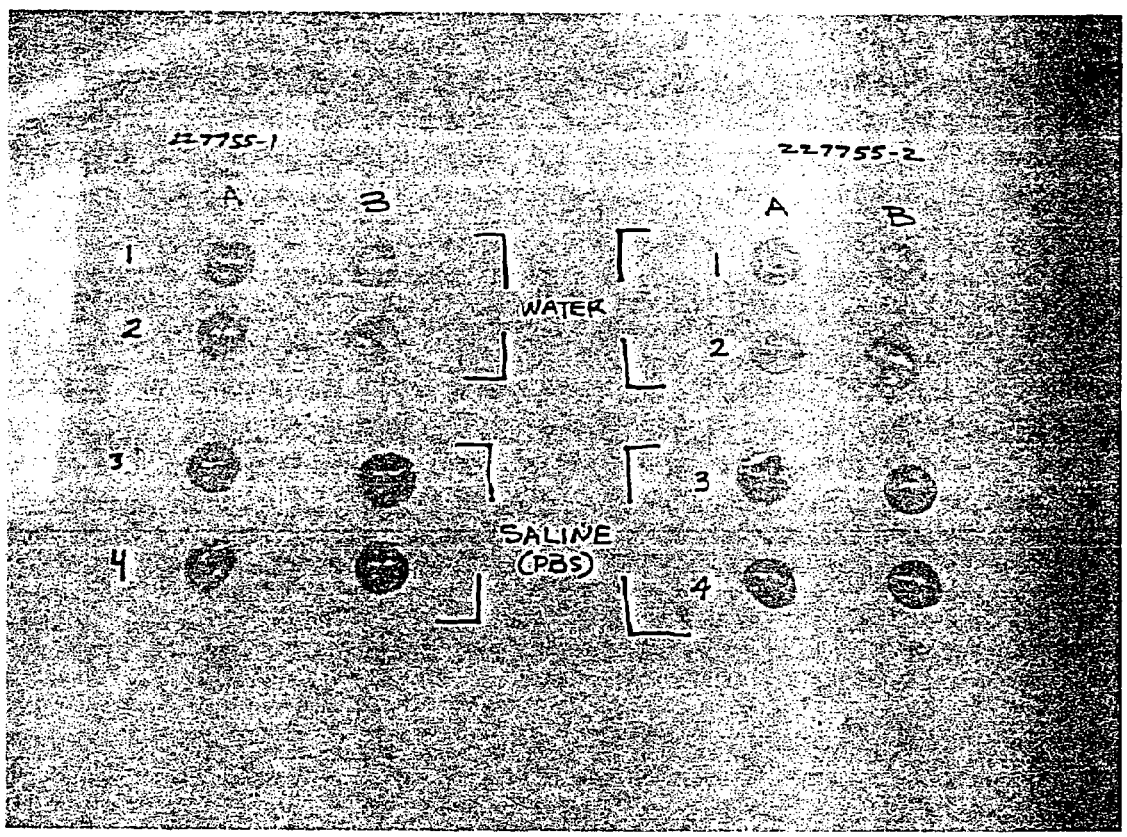
FIG. 1 shows uptake of Rose Bengal by LbL coated lenses.

In general, the present invention is directed to a method for forming on a medical device, preferably an ophthalmic lens, more preferably a contact lens, a diffusion-controllable coating. Such diffusion-controllable coating is capable of controlling the out-diffusion or release of guest materials from the medical device.

A "medical device" refers to a device having surfaces that contact tissue, blood, or other bodily fluids of patients in the course of their operation. Exemplary medical devices include: (1) extracorporeal devices for use in surgery such as blood oxygenators, blood pumps, blood sensors, tubing used to carry blood and the like which contact blood which is then returned to the patient; (2) prostheses implanted in a human or animal body such as vascular grafts, stents, pacemaker leads, heart valves, and the like that are implanted in blood vessels or in the heart; (3) devices for temporary intravascular use such as catheters, guide wires, and the like which are placed into blood vessels or the heart for purposes of monitoring or repair; and (4) ophthalmic devices.

"An ophthalmic device", as used herein, refers to a contact lens (hard or soft), an intraocular lens, a corneal onlay, and other ophthalmic devices (e.g., stents, or the like) used on or about the eye or ocular vicinity.

"Guest materials" as used herein refer to materials which are associated with or entrapped in or bound to a medical device. Exemplary guest materials include, without limitation, materials that impart desired functionalities to a medical device, for example, fluorescently labeled glucose receptor and the fluorescently labeled glucose competitor in ocular glucose sensors disclosed in March's PCT International Publication WO 01/13783, drugs, and monomers and macromer which are not polymerized during the curing process for making the medical device, such as ophthalmic lens.

A "monomer" means a low molecular weight compound that can be polymerized. Low molecular weight typically means average molecular weights less than 700 Daltons.

A "macromer" means a compound or polymer having number average molecular weights greater than 700 and containing functional groups capable of further polymerization.

As used herein the term "drugs" includes medicaments, therapeutics, vitamins, nutritional supplements, and the like. Any pharmaceutical drug can be utilized such as, for example, anti cancer drugs, drug for central nerves, drugs for peripheral nerve, drugs for allergy, drugs for circulatory organs, drugs for respiratory organs, drugs for digestive organs, hormone drugs, antibiotics, drugs for chemotherapy, vitamins, food supplements and the like.

Guest materials, such as drugs, can be adsorbed onto or covalently bound to or entrapped in a medical device and then released from the medical device once it is in contact with a body fluid. If the drug is covalently linked to the medical device or a carrier coated onto the medical device, it is released by enzymatic cleavage (hydrolysis). Alternatively, the entrapped or adsorbed drug is then released from the medical device after in contact with a body fluid.

Entrapment of a guest material, such as a drug, in an ophthalmic lens can be achieved, for example, by first incorporating the drug into a polymerizable composition and then curing the polymerizable composition containing the drug into an ophthalmic lens.

It is found that release of guest materials from a medical device can be controlled by forming a diffusion-controllable coating of the invention on the medical device. The guest material is present in amounts effective for its function. For example, if the guest material is a drug, it is present in therapeutically effective amounts relative to its function.

A "diffusion-controllable coating" refers to a coating which can control out-diffusion or out-flow or release of guest materials from a medical device or prevent guest materials from leaching out of the core of a medical device.

A diffusion-controllable coating of the present invention comprises a layer of clay and optionally one or more layers of polyionic materials.

"Clay" refers to a fine-grained minerals, which is plastic when wet and comprises ydrated silicates of aluminium, such as that term is known in the art. Clay generally has a grain-size of less than ½₂₅₆ mm. The particles of clay are thin sheets with the thickness of about 1 nm and lateral dimensions of about 50-1000 nm. They can form aqueous dispersions in water which are stable for a relatively long period of time. Other materials with similar properties may be utilized in the LBL process described in the present patent. A preferred clay is montmorillonite.

Alternatively, a diffusion-controllable coating of the present invention comprises at least one layer of a first polyionic material and at least one layer of a second polyionic material having charges opposite of the charges of the first polyionic material. The diffusion-controllable coating of the present invention preferably comprises 2-30 layers of each of the first and second polyionic materials, more preferably 2-15 layers of each of the first and second polyionic materials, even more preferably 2-6 layers of each of the first and second polyionic materials.

A diffusion-controllable coating of the invention can be formed on the untreated surface or treated surface of a medical device. A "treated surface" refers to a surface of a medical device which has been treated, functionalized, coated or modified according to a known procedure prior to formation thereon of the diffusion-controllable coating. Exemplary surface treatments or modifications include, without limitation, plasma treatment, chemical modification or functionalization, plasma coating, LbL coating, and the like.

For example, if the surface of a medical device has hydroxy groups, the support may be placed in a bath of an innert solvent, such as tetrahydrofuran, and tresyl chloride. The hydroxy groups on the surface are then tresylated. Once tresylated, the surface may be aminated in a water solution of ethylene diamine, which results in bonding the group —NH—CH$_2$—CH$_2$—NH$_2$ to the carbon atom thereon. Alternatively, for example, a contact lens made from a hydrogel, can be dipped into or sprayed with a solution containing a diaziridine compound, which is subsequently attached covalently to the surface of the contact lens via a thermal process, so as to functionalize the contact lens. Such functionalized lenses can be used in covalently attaching guest materials or polyionic materials to the functionalized lens.

Once the desired coating is applied to a contact lens, the coating can, in some embodiments, be cross-linked to make the surface even more resistant to wear or abrasion, as well as more durable. The coating can generally be cross-linked by any method known in the art. For example, in one embodiment, a crosslinking agent can be sprayed onto the coating and, thereafter, radiation with visible light can then be applied such that the coating becomes cross-linked. Suitable crosslinking agents can include, for example, active moieties such as carbenes, nitrenes, and the like.

As used herein, a "polyionic material" refers to a polymeric material that has a plurality of charged groups, such as polyelectrolytes, p- and n-type doped conducting polymers. Polyionic materials include both polycationic (having positive charges) and polyanionic (having negative charges) materials.

A polycationic material used in the present invention can generally include any material known in the art to have a plurality of positively charged groups along a polymer chain. For instance, suitable examples of such polycationic materials can include, but are not limited to, poly(allylamine hydrochloride) (PAH), poly(ethyleneimine) (PEI), poly(vinylbenzyltriamethylamine) (PVBT), polyaniline (PAN or PANI) (p-type doped) [or sulphonated polyaniline], polypyrrole (PPY) (p-typed doped), and poly(pyridinium acetylene).

A polycationic material used in the present invention can also include polymeric quaternary ammonium compounds (polyquats). When polyquats are used in the coating of an ophthalmic lens, they may impart antimicrobial properties to the ophthalmic lens.

A polyanionic material used in the present invention can generally include any material known in the art to have a plurality of negatively charged groups along a polymer chain. For example, suitable polyanionic materials can include, but are not limited to, polymethacrylic acid (PMA), polyacrylic acid (PAA), poly(thiophene-3-acetic acid) (PTAA), poly(4-styrenesulfonic acid) (PSS), sodium poly(styrene sulfonate) (SPS) and poly(sodium styrene sulfonate) (PSSS).

The foregoing lists are intended to be exemplary, but clearly are not exhaustive. A person skilled in the art, given the disclosure and teaching herein, would be able to select a number of other useful polyionic materials.

In order to alter various characteristics of the coating, such as thickness, the molecular weight of the polyionic materials can be varied. In particular, as the molecular weight is increased, the coating thickness generally increases. However, if the increase in molecular weight increase is too substantial, the difficulty in handling may also increase. As such, polyionic materials used in a process of the present invention will typically have a molecular weight $M_n$ of about 2,000 to about 150,000. In some embodiments, the molecular weight is about 5,000 to about 100,000, and in other embodiments, from about 75,000 to about 100,000.

A diffusion-controllable coating on a medical device can be prepared, in one embodiment, by applying a layer of clay and at least one layer of polyionic material onto the surface of the medical device. The medical device is preferably an ophthalmic lens, more preferably a contact lens. The clay is preferably montmorillonite. Any known suitable method of coating a layer of clay onto a medical device can be used. One preferred procedure is shown in Example 6.

Application of a layer of polyionic material may be accomplished in a number of ways as described in pending U.S. patent application Ser. Nos. 09/005,317, 09/774,942, 09/775, 104, which are commonly owned with the instant invention and are herein incorporated by reference in their entireties. One coating process embodiment involves solely dip-coating and dip-rinsing steps. Another coating process embodiment involves solely spray-coating and spray-rinsing steps. However, a number of alternatives involves various combinations of spray- and dip-coating and rinsing steps may be designed by a person having ordinary skill in the art.

A diffusion-controllable coating on a medical device can be prepared, in another embodiment, by: (1) applying alternatively a layer of a first polyionic material and a layer of a second polyionic material having charges opposite of the charges of the first polyionic material; (2) releasing the coated medical device into a releasing medium having a composition capable of imparting a desired permeability to the diffusion-controllable coating on the medical device.

"A releasing medium" or "a releasing and storage medium" as used herein refers to water or a solution into which a medical device is released and stored after coating of the final layer of polyionic material onto the medical device.

It has been found by the inventors that the properties of LbL coating can be manipulated by changing the composition of a releasing and storage medium. Using different releasing and storage media, for example, water or phosphate buffer (PBS), the coating properties (permeability, wettability, thickness, composition, etc.) can be controlled. When using water as releasing and storage medium, LbL coatings on lenses appear to be dense/compact and have lower permeability. When using PBS as releasing and storage medium, LbL coatings on lenses appear to be more loose/fluffy and have higher permeability. Based on contact angle, LbL coatings on lenses are more wettable when using water as releasing and storage medium than when using PBS as releasing and storage medium. It has been also found that the thickness of LbL coatings on silicon wafer may depend upon the composition of a releasing and storage medium. These findings will allow to tailor coatings with desired properties on any medical device, which will have many applications such as controlled release of different moieties (drug, nutrients, lubricants, etc), and control of out-diffusion of low or high molecular weight moieties, etc.

"LbL coating", as used herein, refers to a layer-by-layer ("LbL") deposition of polyelectrolytes on an article. Any suitable LbL polyelectrolyte deposition techniques can be used in the LbL coating. For example, a pending U.S. patent application Ser. No. 09/199,609, filed on Nov. 25, 1998 and commonly owned with the instant invention, discloses an LbL polyelectrolyte deposition technique that involves consecutively dipping a substrate into oppositely charged polyionic materials until a coating of a desired thickness is formed. LbL coatings can also be asymmetrical. As used herein, "asymmetrical coatings" on an ophthalmic lens refers to the different coatings on the first surface and the opposite second surface of the ophthalmic lens. As used herein, "different coatings" refers to two coatings that have different surface properties or functionalities.

In a preferred embodiment, the releasing medium is pure water which is capable of producing a LbL coating having a minimal permeability characterized by negligible uptake of Rose Bengal by the medical device.

In another preferred embodiment, the releasing medium is a phosphate buffer capable of producing a LbL coating having a higher permeability characterized by a noticeable uptake of Rose Bengal by the medical device.

It has been discovered and disclosed in U.S. application Ser. No. 09/005,317, commonly owned with the instant invention, that complex and time-consuming pretreatment of a core material (medical device) is not required prior to binding of a polyionic material to the core material. By simply contacting a core material of a medical device, for example, a contact lens, with one or more solutions each containing one or more polyionic materials, an LbL coating can be formed on a medical device to modify the surface properties of the core material of the medical device. An LbL coating can be a single layer or a bilayer or multiple bilayers.

Application of an LbL coating may be accomplished in a number of ways as described in pending U.S. patent application Ser. Nos. 09/005,317, 09/774,942, 09/775,104, which are commonly owned with the instant invention and herein incorporated by reference in their entireties. One coating process embodiment involves solely dip-coating and dip-rinsing steps. Another coating process embodiment involves solely spray-coating and spray-rinsing steps. However, a number of alternatives involve various combinations of spray- and dip-coating and rinsing steps may be designed by a person having ordinary skill in the art.

One dip-coating alternative involves the steps of applying a coating of a first polyionic material to a core material of a medical device by immersing said medical device in a first solution of a first polyionic material; rinsing the medical device by immersing the medical device in a rinsing solution; and, optionally, drying the medical device. This procedure can be repeated using a second polyionic material, with the second polyionic material having charges opposite of the charges of the first polyionic material, in order to form a polyionic bilayer. This bilayer formation process may be repeated a plurality of times in order to produce a thicker LbL coating. A preferred number of bilayers is about 5 to about 20 bilayers. While more than 20 bilayers are possible, it has been found that delamination may occur in some LbL coatings having an excessive number of bilayers.

The immersion time for each of the coating and rinsing steps may vary depending on a number of factors. Preferably, immersion of the core material into the polyionic solution occurs over a period of about 1 to 30 minutes, more preferably about 2 to 20 minutes, and most preferably about 1 to 5 minutes. Rinsing may be accomplished in one step, but a plurality of rinsing steps can be quite efficient.

Another embodiment of the coating process is a single dip-coating process as described in U.S. application Ser. No. 09/775,104, herein incorporated by reference in its entirety. Such single dip-coating process involves dipping a core material of a medical device in a solution containing a negatively charged polyionic material and a positively charged polyionic material in an amount such that the molar charge ratio of said solution is from about 3:1 to about 100:1. Multiple bilayers can be formed on a medical device by using this single dip-coating process.

Another embodiment of the coating process involves a series of spray coating techniques. The process generally includes the steps of applying a coating of a first polyionic material to a core material of a medical device with a first solution of a first polyionic material; rinsing the medical device by spraying the medical device with a rinsing solution; and optionally, drying the medical device. Similar to the dip-coating process, the spray-coating process may be repeated with a second polyionic material, with the second polyionic material having charges opposite of the charges of the first polyionic material.

The contacting of the medical device with solution, either polyionic material or rinsing solution, may occur by a variety of methods. For example, the medical device may be dipped into both solutions. One preferred alternative is to apply the solutions in a spray or mist form. Of course, various combinations may be envisioned, e.g., dipping the medical device in the polyionic material followed by spraying the rinsing solution.

The spray coating application may be accomplished via a number of methods. For example, a conventional spray coating arrangement may be used, i.e., the liquid material is sprayed by application of fluid, which may or may not be at elevated pressure, through a reduced diameter nozzle which is directed towards the deposition target.

Preferably, a spraying process is selected from the group consisting of an air-assisted atomization and dispensing process, an ultrasonic-assisted atomization and dispensing process, a piezoelectric assisted atomization and dispensing process, an electro-mechanical jet printing process, a piezo-electric jet printing process, a piezo-electric with hydrostatic pressure jet printing process, and a thermal jet printing process; and a computer system capable of controlling the positioning of the dispensing head of the spraying device on the ophthalmic lens and dispensing the coating liquid. Those spraying coating processes are described in U.S. Application No. 60/312,199, herein incorporated by reference in its entirety. By using such spraying coating processes, an asymmetrical coating can be applied to a medical device. For example, the back surface of a contact lens can be coated with a hydrophilic and/or lubricous coating material and the front surface of the contact lens can be coated with an antimicrobial material. It is also possible to produce a coating on a contact lens, the coating having a functional pattern so as to provide simultaneously multiple benefits to a wearer.

In accordance with the present invention, polyionic material solutions can be prepared in a variety of ways. In particular, a polyionic solution of the present invention can be formed by dissolving the polyionic material(s) in water or any other solvent capable of dissolving the materials. When a solvent is used, any solvent that can allow the components within the solution to remain stable in water is suitable. For example, an alcohol-based solvent can be used. Suitable alcohols can include, but are not limited to, isopropyl alcohol, hexanol, ethanol, etc. It should be understood that other solvents commonly used in the art can also be suitably used in the present invention.

Whether dissolved in water or in a solvent, the concentration of a polyionic material in a solution of the present invention can generally vary depending on the particular materials being utilized, the desired coating thickness, and a number of other factors. However, it may be typical to formulate a relatively dilute aqueous solution of polyionic material. For example, a polyionic material concentration can be between about 0.001% to about 0.25% by weight, between about 0.005% to about 0.10% by weight, or between about 0.01% to about 0.05% by weight.

In general, the polyionic solutions mentioned above can be prepared by any method well known in the art for preparing solutions. For example, in one embodiment, a polyanionic solution can be prepared by dissolving a suitable amount of the polyanionic material, such as polyacrylic acid having a molecular weight of about 90,000, in water such that a solution having a certain concentration is formed. In one embodiment, the resulting solution is a 0.001M PAA solution. Once dissolved, the pH of the polyanionic solution can also be adjusted by adding a basic or acidic material. In the embodiment above, for example, a suitable amount of 1N hydrochloric acid (HCl) can be added to adjust the pH to 2.5.

Polycationic solutions can also be formed in a manner as described above. For example, in one embodiment, poly(allylamine hydrochloride) having a molecular weight of about 50,000 to about 65,000 can be dissolved in water to form a 0.001M PAH solution. Thereafter, the pH can also be adjusted to 2.5 by adding a suitable amount of hydrochloric acid.

In some embodiments of the present invention, it may be desirable to apply a solution containing both polyanionic and polycationic materials within a single solution. For example, a polyanionic solution can be formed as described above, and then mixed with a polycationic solution that is also formed as described above. In one embodiment, the solutions can then be mixed slowly to form the coating solution. The amount of each solution applied to the mix depends on the molar charge ratio desired. For example, if a 10:1 (polyanion:polycation) solution is desired, 1 part (by volume) of the PAH solution can be mixed into 10 parts of the PAA solution. After mixing, the solution can also be filtered if desired.

It is discovered that a very "flat", dense bilayer coating on a medical device can be prepared from a relatively low molecular weight, preferably 50,000 to 300,000 weak polyacid (polyanion) at a low pH (i.e. 2.5) with a low molecular weight preferably 50,000 to 300,000 weak polybase (polycation) at similar pH. The density of the coating would be a function of pH and molecular weight. By using a relatively low molecular weight weak polyacid without long polymeric side-chain and a low molecular weight weak polybase without long polymeric side-chain, a diffusion-controllable coating having permeability similar to the permeability of a clay layer can be formed on a medical device at a pH of from about 1.5 to about 8.5.

A preferred embodiment of the polyionic materials for making a LbL coating are a weak polyacid having relatively low molecular weight and a weak polybase having relatively low molecular weight. Preferably, the polyacid and polybase solutions have a pH of from about 1.5 to about 8.5.

The diffusion-controllable coating and methods for making the same on an ophthalmic lens can find use in minimizing guest materials leaching out of medical devices, as described in Examples 5 and 6.

The diffusion-controllable coating and methods for making the same on an ophthalmic lens can also find use in controlled release of lubricants to a contact lens surface for improved comfort and in controlled delivery of therapeutic agents in a continuous manner or in a triggerable manner in response to physiological conditions (smart LbL coatings).

For example, A mucin-like material, e.g., polyglycolic acid, polylactides, collagen or gelatin, can be used as guest materials which can be released continuously and slowly over extended period of time to the ocular surface of the eye for treating dry eye syndrome. The mucin-like material preferably is present in the diffusion-controllable coating in effective amounts.

Under normal conditions, ocular fluid forms a thin layer (tear film) approximately 7-10 micrometers thick that covers the corneal and conjunctival epithelium. This ultra thin layer provides a smooth optical surface to the cornea by abolishing minute surface irregularities of its epithelium, wets the surface of the corneal and conjuctival epithelium, thereby preventing damage to the epithelial cells, and inhibits the growth of microorganisms on the conjunctiva in the cornea by mechanical flushing.

The tear film normally includes a three layer structure. The outermost layer is a lipid layer derived from the secretions of the meibomian glands and thought to retard evaporation of the aqueous layer. The middle aqueous layer is provided by the major and minor lacrimal glands, and contains water-soluble substances. The innermost mucinous layer is composed of glycoprotein, mucin, and overlies the corneal and conjunctival epithelial cells. The epithelial cell membranes are composed of lipoproteins and thus generally hydrophobic. The mucin plays an important role in wetting the surface. Under normal conditions, mucin is provided by goblet cells of the conjunctiva and is also provided from the lacrimal gland.

When any of the tear film components is deficient, the tear film will break up, and dry spots will form on the corneal and the conjunctival epithelium. Deficiency of any of the three components (aqueous, mucin or lipid) may result in dryness of the eye.

When the contact lens containing the mucin-like material in mucin-like material in an effective amount is inserted into the eye, the mucin-like material is released from the contact lens into the eye under control of a diffusion-controllable coating on the contact lens and wets the eye.

Another example is that antimicrobial agents may be adsorbed onto or entrapped in a biomedical device. In this way, if the biomedical device contains an antimicrobial agent, the contamination of the biomedical device, e.g., contact lens or intraocular lens, by microbes, e.g., bacteria, is reduced relative to a contact lens wherein the antimicrobial agent is absent. The antimicrobial agent is present in an amount sufficient to retard and/or substantially prevent contamination by the microbe.

The diffusion-controllable coating and methods for making the same on an ophthalmic lens can also find use in eliminating an extraction process in the manufacturing of ophthalmic lenses. An "extraction process" as used herein refers to a step of a manufacturing process of an ophthalmic lens, where unpolymerized materials are removed from the core of the ophthalmic lens by application of a solvent.

The present invention provides a cost effective method of manufacturing ophthalmic lenses comprising: (1) producing the ophthalmic lenses by molding in molds or by lathing and (2) forming a diffusion-controllable coating on each of the ophthalmic lenses produced in step (1) by a) applying one layer of clay and optionally one or more layers of polyionic materials onto the medical device or b) applying alternatively a layer of a first polyionic material and a layer of a second polyionic material having charges opposite of the charges of the first polyionic material onto the medical device and releasing the coated medical device into a releasing medium having a composition capable of imparting a desired permeability to the diffusion-controllable coating on the medical device.

The previous disclosure will enable one having ordinary skill in the art to practice the invention. In order to better enable the reader to understand specific embodiments and the advantages thereof, reference to the following non-limiting examples is suggested. However, the following examples should not be read to limit the scope of the invention.

EXAMPLE 1

Coating of Silicon Wafers and Contact Lenses by LbL

LbL coatings on silicon wafers or contact lenses are carried as follows. A silicon wafer is dipped first into a first coating solution containing the first polyelectrolyte for about 5 minutes and then into a second coating solution containing a second polyelectrolyte having charges opposite to the first polyelectrolyte for about 5 minutes. A rinsing step can be carried out between the dips in the first and second coating solutions. This procedure of dipping in an alternative fashion into the first and second coating solutions can be repeated for a number of times. After a final layer of polyelectrolytes is coated on the wafer, the coated wafer is then released into a releasing and storage medium (e.g., pure water or PBS) where the coated wafers are stored.

LbL coatings on contact lenses are carried as follows. A contact lens is dipped first into a first coating solution containing a first polyelectrolytes and then into a second coating solution containing a second polyelectrolyte having charges opposite to the first polyelectrolyte. The time for coating the first layer of polyelectrolytes is about five minutes. The time for coating the second and subsequent layers of polyelectrolytes is also about five minutes. A rinsing step may be carried out between the dips in the first and second coating solutions. This procedure of dipping in an alternative fashion into the first and second coating solutions can be repeated for a number of times. After a final layer of polyelectrolytes is coated on the lens, the coated lens is then released into a releasing and storage medium (e.g., pure water or PBS) where the coated lens are stored.

EXAMPLE 2

Preparation of Coating Solutions

S1: S1 is prepared by mixing a polyacrylic acid (PAA) solution ([PAA]=0.001 M, pH 2.5) with a polyallylamine hydrochloride (PAH) solution ([PAH]=0.001 M, pH 2.5) in a ratio of 10/1 (PAA/PAH) by volume.

S2: S2 is prepared by mixing a PAH solution ([PAH]=0.001 M, pH 2.5) with a PAA solution ([PAA]=0.001 M, pH 2.5) in a ratio of 10/1 (PAH/PAA) by volume.

S2A: S2A is prepared by mixing a PAH solution ([PAH]=0.001 M, pH 4.5) with a PAA solution ([PAA]=0.001 M, pH 4.5) in a ratio of 10/1 (PAH/PAA) by volume.

S3: S3 is prepared by dissolving an amount of PAA in water to have [PAA]=0.01 M. pH of the solution is adjusted to pH 3.5.

S3A: S3A is prepared by dissolving an amount of PAA in water to have [PAA]=0.01 M. pH of the solution is adjusted to pH 2.5.

S4: S4 is prepared by dissolving an amount of PAH in water to have [PAH]=0.01 M. pH of the solution is adjusted to pH 7.5.

S4A: S4A is prepared by dissolving an amount of PAH in water to have [PAH]=0.01 M. pH of the solution is adjusted to pH 4.5.

S4B: S4B is prepared by dissolving an amount of PAH in water to have [PAH]=0.01 M. pH of the solution is adjusted to pH 3.5.

S5: S5 is prepared by dissolving an amount of PAA in water to have [PAA]=0.001 M. pH of the solution is adjusted to pH 3.5.

S6: S6 is prepared by dissolving an amount of PAH in water to have [PAH]=0.001 M. pH of the solution is adjusted to pH 4.6.

S7: S7 is prepared by dissolving 0.72 g PAAm-co-PAA (30/70) in one liter of water. pH=3.5.

S8: S8 is prepared by dissolving 0.72 g PAAm-co-PAA, (30/70) in one liter of water. pH=4.5.

PBS: 7.89 grams of NaCl, 0.7733 grams of $NaH_2PO_4$ and 4.759 grams of $Na_2HPO_4$ are dissolved in one liter of water. pH of the solution is about 7.2 to 7.4.

EXAMPLE 3

Characterization of LbL Coatings on Silicon Wafers

Silicon wafers are coated under a variety of coating conditions according to the LbL coating procedure described in Example 1.

The thickness of coatings on silicon wafers is measured by ellipsometry to determine the effects of coating conditions and releasing media on the thickness of coatings. Results are reported in Table 1.

For coating lot #217930 (Table 1), the thickness of coatings remains to be the same for silicon wafers in water and in PBS. For other coating lots listed in Table 1, the thickness of coatings changes significantly with different releasing media. It is discovered here that using different releasing media for LbL coatings is one of ways to control the coating thickness.

TABLE 1

Thickness of various coatings on Silicon wafers in water and in PBS

| Coating Lot # | Coating | Number of dips | Rinsing | Thickness*[1] (H2O) | Thickness*[2] (PBS) |
|---|---|---|---|---|---|
| 213469-10S | (S1/S2) × 5 | 10 | yes | 145.2 ± 12.1 | 71.7 ± 3.9 |
| 213469-16S | (S1/S2) × 8 | 16 | yes | 310.5 ± 25.0 | 99.8 ± 18.9 |
| 217933-1 | (S2A/S1) × 4 | 8 | no | 231.9 ± 15.5 | 35.1 ± 9.2 |
| 217933-2 | (S2A/S1) × 4 | 8 | yes | 142.7 ± 31 | 34.2 ± 7.2 |
| 217930 | (S3/S4) × 10//S3 | 21 | yes | 846.3 ± 47.1 | 846.0 ± 39.1 |
| 217931-1Si | (S6/S5) × 4 | 8 | no | 222.8 ± 31.6 | 58.0 ± 20.7 |
| 217931-2Si | (S6/S5) × 8 | 16 | no | 508.3 ± 46.1 | 115.3 ± 65.0 |

*Averaged value with an angstrom unit (Å) from 10 data points in most cases.
[1]Coated wafers are released directly into water and stored in water.
[2]Coated wafers are released directly into PBS and stored in PBS.

The surface composition of coatings on silicon wafer is determined by x-ray photoelectron spectroscopy (XPS) to determine the effects of coating conditions and releasing media on the thickness of coatings. Results are reported in Table 2.

TABLE 2

Surface composition of silicon wafers stored in water and in PBS

| Coating Lot # | Releasing Medium | Sampling depth (nm) | C % | O % | Si % | N % |
|---|---|---|---|---|---|---|
| Uncoated Si* | / | 2 | 40.8 | 30.8 | 24.3 | 0.6 |
| 222537-3Si* | PBS | 2 | 46.6 | 29.3 | 21.0 | 0.7 |
| 223157 | water | 2 | 63.0 | 26.0 | 6.4 | 3.0 |
| Uncoated Si | / | 10 | 14.0 | 28.6 | 55.0 | 0.4 |
| 222537-3Si* | PBS | 10 | 20.4 | 28.8 | 48.8 | 0.5 |
| 223157* | water | 10 | 42.9 | 26.5 | 27.7 | 1.9 |

*Coating condition: 9 dips, S1/(S2A/S1) × 4.

The surface composition of coatings obtained under the coating conditions in the study can be affected by releasing media (Table 2). It is discovered here that using different releasing media for LbL coatings is one of ways to control the surface composition of the coatings.

EXAMPLE 4

Characterization of LbL Coatings on Contact Lenses

Contact lenses are coated under a variety of coating conditions according to the LbL coating procedure described in Example 1.

Surface Composition

The surface composition of coatings on contact lenses is determined by x-ray photoelectron spectroscopy (XPS) to determine the effects of coating conditions and releasing media on the thickness of coatings. Results are reported in Table 3 and indicate that the surface composition is independent of releasing media (in water vs. in PBS).

TABLE 3

Surface composition of coated lenses (in water vs. in PBS)

| Coating Lot # | Releasing Medium | Samping depth (nm) | C % | O % | Si % | N % | F % | Na % |
|---|---|---|---|---|---|---|---|---|
| 226699C* | / | 5~8 | 55.2 | 20.0 | 12.5 | 5.0 | 7.4 | 0 |
| 226699W** | water | 5~8 | 57.3 | 19.9 | 11.4 | 4.4 | 7.0 | 0 |
| 226699S | PBS | 5~8 | 57.0 | 21.2 | 10.6 | 4.4 | 6.3 | 0.6 |

*Uncoated lens as control
**Coating condition: 9 dips, S1/(S2A/S1) × 4.

Permeability

The permeability of coated lenses are estimated by measuring visually and spectroscopically the interaction (diffusion/penetration into the coatings) of Rose Bengal with LbL coatings. Dependency of the permeability of the coatings on releasing media (e.g., water vs. PBS) is studied. Rose Bengal, an anionic pink dye, will preferentially interact with the positive surface/domain of LbL coatings and render the clear lenses pink in color. When using water as the releasing medium, coated lenses remains to be clear, indicating no or minimal uptake of Rose Bengal dyes by coated lenses (FIG. 1). In contrast, when using PBS as the releasing medium, coated lenses become pink, indicating uptake of Rose Bengal dyes by coated lenses (FIG. 1). This observation lead us to believe that when using water as releasing medium the LbL coatings on contact lenses appear to be dense/compact and have lower permeability, whereas when using PBS as releasing medium the LbL coatings on coated lenses appear to be more loose/fluffy and have higher permeability.

The dependency of the permeability of coatings on contact lenses on releasing media is also confirmed by UV spectroscopic measurements. After being up-taken by the lenses, the Rose Bengal in lenses has a WV absorption peak at 565 nm. The higher the absorbance, the more the uptake of the rose Bengal, and the higher the permeability. In the case where water is used as releasing medium, the absorbance is zero or close to zero (depending on the concentration of Rose Bengal, and also the nature of the outmost layer of the LbL coating, see attached file). In the case where PBS is used as releasing medium, the absorbance can be as high as 0.2 (Table 4). Effects of autoclave on permeability of coatings are also tested and the results are shown in Table 4.

TABLE 4

UV absorbance at 565 nm of Rose Bengal uptake by lenses.

| Lot # | Coating conditions | Medium | Autoclave | [RB] (mg/L) | Absorbance at 365 nm |
|---|---|---|---|---|---|
| 227755-1 | (PAA/PAH) × 4/PAA | water | No | 10 | 0 |
| | | water | yes | 10 | 0 |
| | | PBS | no | 10 | 0.020 |
| | | PBS | yes | 10 | 0.015 |
| 227755-2 | (PAA/PAH) × 4/PAA/PAH | water | No | 10 | 0 |
| | | water | yes | 10 | 0 |
| | | PBS | no | 10 | 0.020 |
| | | PBS | yes | 10 | 0.017 |
| 227755-1 | (PAA/PAH) × 4/PAA | water | No | 100 | 0.05 |
| | | water | yes | 100 | 0 |
| | | PBS | no | 100 | 0.18 |
| | | PBS | yes | 100 | 0.16 |
| 227755-2 | (PAA/PAH) × 4/PAA/PAH | water | No | 100 | 0.023 |
| | | water | yes | 100 | 0.014 |
| | | PBS | no | 100 | 0.20 |
| | | PBS | yes | 100 | 0.19 |

The permeability of coatings on lenses is higher when using PBS as releasing medium than when using water as releasing medium, as demonstrated by differential penetration of dye molecule into the coatings and differential diffusion of molecules out of the coatings. It is discovered here that the coating properties can be controlled using different releasing and storage media.

Wettability

The wetting angle (contact angle) on coated lenses depends on the releasing media used in the final step of coating processes. It is generally lower when using water as releasing medium (Table 5).

It is discovered unexpected that the LbL coated lenses appear to be more wettable (significantly lower water contact angle) if autoclaved in ultra-pure water as compared to lenses autoclaved in PBS (Table 5). For example, for lenses lot #222513-1, the contact angle is zero (or too low to be measured) for lenses autoclaved in water and 50 for lenses autoclaved in PBS. If the lenses are first autoclaved in water and then autoclaved in PBS, the contact angle does not change. For example, the contact angle remains to be 32 degrees for lenses autoclaved in water and for lenses autoclaved in water and then in PBS.

TABLE 5

Contact angles (water) on LbL coated lenses

| Coating Lot # | Coating | No. of dips | Water rinse | Contact angle*[1] | Contact angle*[2] |
|---|---|---|---|---|---|
| 222511-2 222511-2A | S3A/(S4A/ S8) × 5 | 11 | yes | 0 | 28 ± 0.8 |
| 222513-1 222513-1A | S3A/(S4B/ S7) × 5 | 11 | yes | 0 | 50 ± 2.4 |
| 033767 033767yx | S3A/(S1/ S2A) × 4 | 9 | no | 32 ± 9.6** | 88 ± 2.4 |

*Average value from 4 to 6 data points in most cases.
**If autoclaved again in saline, the contact angle remains to be the same (32 ± 4.4).
[1]The releasing medium is water.
[2]The releasing medium is PBS.

EXAMPLE 5

Figure 2:
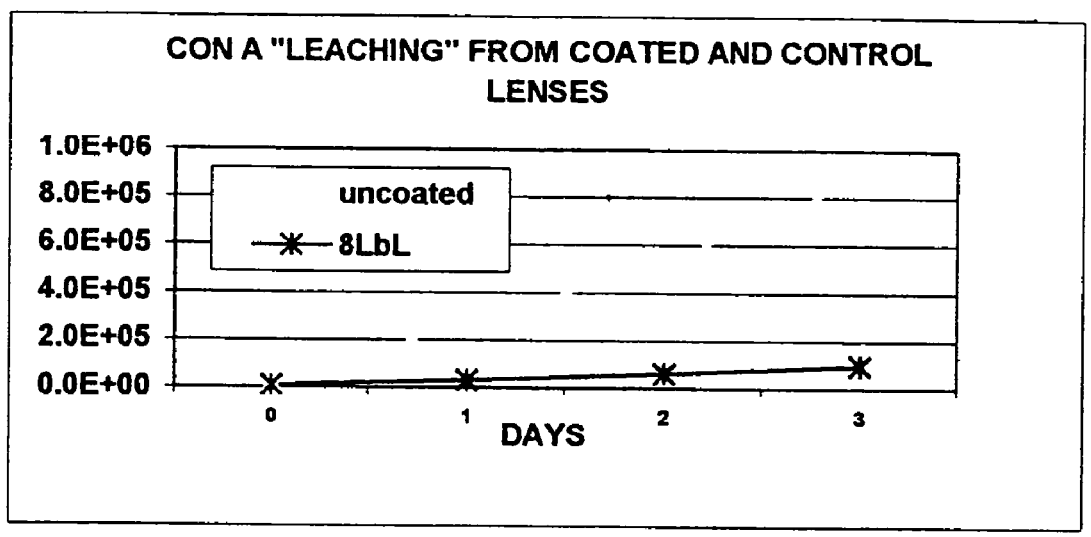
FIG. 2 shows the leaching profile of Con-A from both coated lenses and uncoated (control) lenses.

Contact lenses are prepared using a modified formulation for Dailies™ (CIBA Vision) contact lenses. The modified formulation contains additional materials, Con A-rhodamine and FITC Dextran. The contact lenses are first coated with a layer of polyacrylic acid (PAA, pH2.5). This coating is shown to be adherent to the lenses based on contact angle and toluidine blue dye test. Then a layer of PAA (pH6.5) is applied followed by a layer of PAA (pH 2.5). On top of these three layers, 8 bilayers of polyallylamine hydrochloride (PAH, pH6.5) and PAA (pH6.5) are then placed. The coated lenses are released into and stored in water for further testing. The rate of releasing of the Con A-rhodamine and the FITC-Dextran into a solution are measured by fluorescence spectroscopy. FIG. 2 shows "leaching" profiles of CON A from LbL coated and control lenses as measured by fluorescence spectroscopy. The fluorescence signal intensity remains little changed for coated lenses with LbL coatings, indicating no leaching out of Con A from the coated lenses. However, the signal intensity increases significantly from uncoated control lenses, indicating leaching of Con A from the uncoated control lenses.

The "leaching" profile of Con-A from LbL coated lenses are obtained by monitoring the fluorescence of a solution from a container having 4.6 ml of TRIS buffer with 5 LbL coated lenses therein.

For the control experiment, the data are obtained by monitoring the fluorescence of a solution from a container having 4.6 ml of TRIS buffer with 5 uncoated lenses.

EXAMPLE 6

Contact lenses are prepared using a modified formulation for Dailies™ (CIBA Vision) contact lenses. The modified formulation contains additional materials, Con A-rhodamine and FITC Dextran. The contact lenses are first coated with a layer of montmorillonite (clay) as described below.

Preparation of clay dispersion: Approximately 0.5 grams of clay (montmorillonite) is dispersed in about 100 ml of DI water and ultrasonicated for two hours in a Fisher Scientific FS20 ultrasonicator. The solution is allowed to stand for at least one day and the supernatant is removed. The remaining suspension is diluted with e-pure water at a ratio of about 1:5, or 10 ml diluted to 50 ml, to obtain a dispersion that is not very concentrated as the original suspension which has a high particulate density.

Coating of clay: A layer-by-layer deposition technique is used to apply a coating comprising layers of clay. The layer by layer deposition is achieved based on the mutual attraction of positively charged polyelectrolyte and the clay platelet surface which are essentially negatively charged. First, contact lenses are immersed in a 1% solution (aq) of PDDA (Poly (diallyldimethylammonium chloride) from Aldrich) for five minutes to allow for good adsorption of the polyelectrolyte (PE). The contact lenses are then removed one at a time from the PE solution and briefly rinsed with clean water to remove excess PE. The contact lenses while still wet, are immersed in a clay dispersion for 1-10 minutes to deposit a layer of clay. This coating comprising a layer of clay is shown to be adherent to the lenses and to have a uniform coverage by AFM. Bilayers of poly DADMAC and PAA are then placed on top of the montmorillonite layer.

Figure 3:
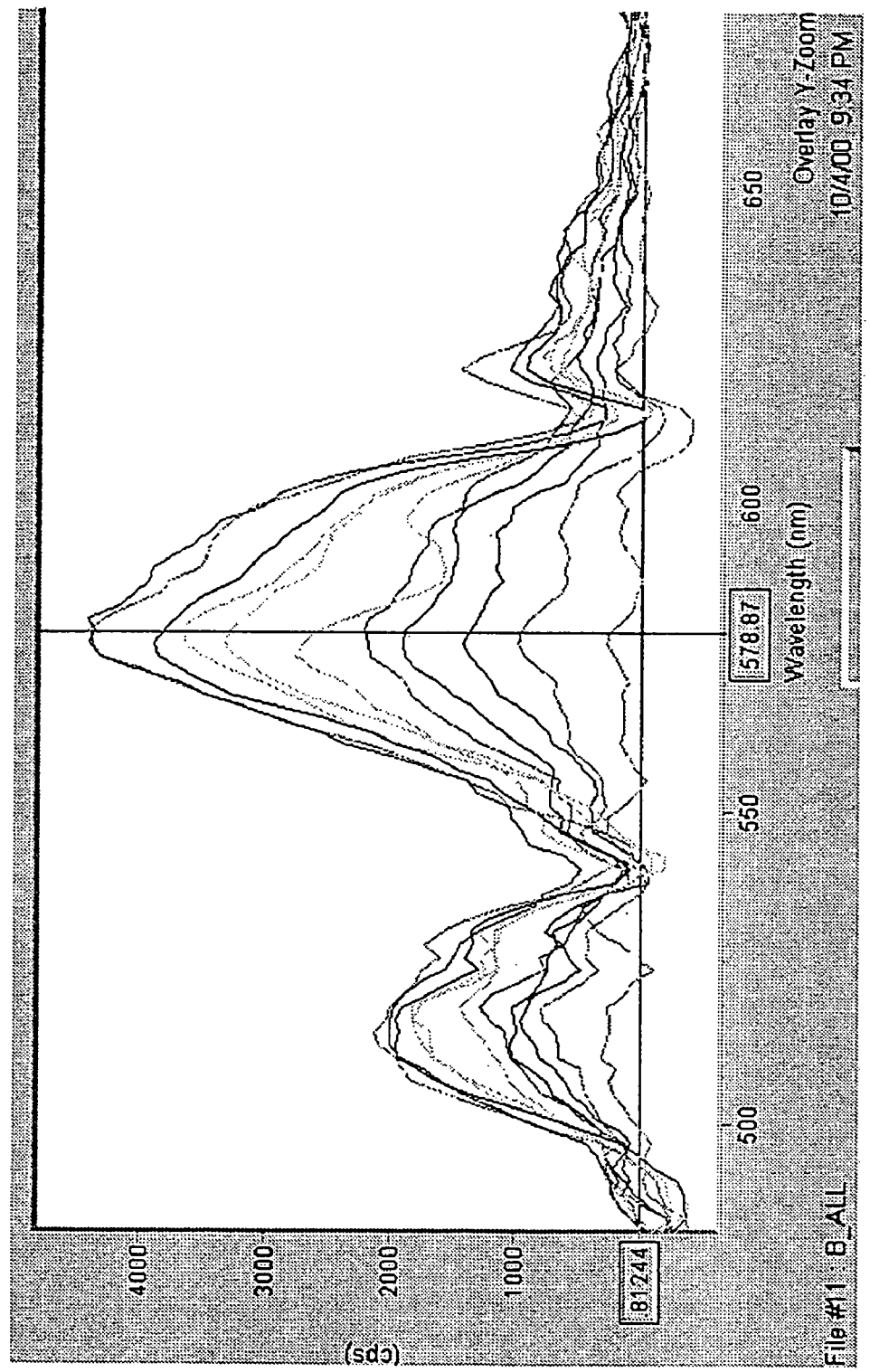
FIG. 3 shows the fluorescence spectra of a solution containing uncoated lenses comprising fluorescently labeled Con-A and Dextran as a function of time.
Figure 4:
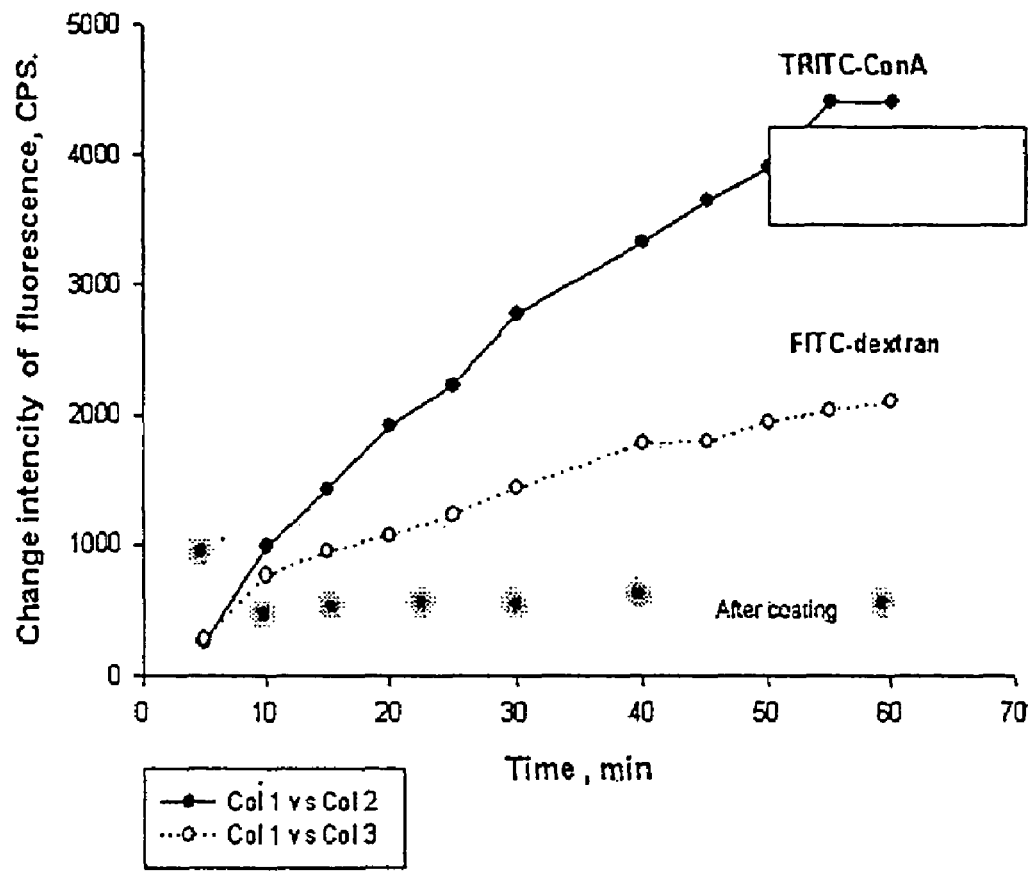
FIG. 4 shows outflow dynamics of the fluorescently labeled Con-A and Dextran from uncoated lenses.
Figure 5:
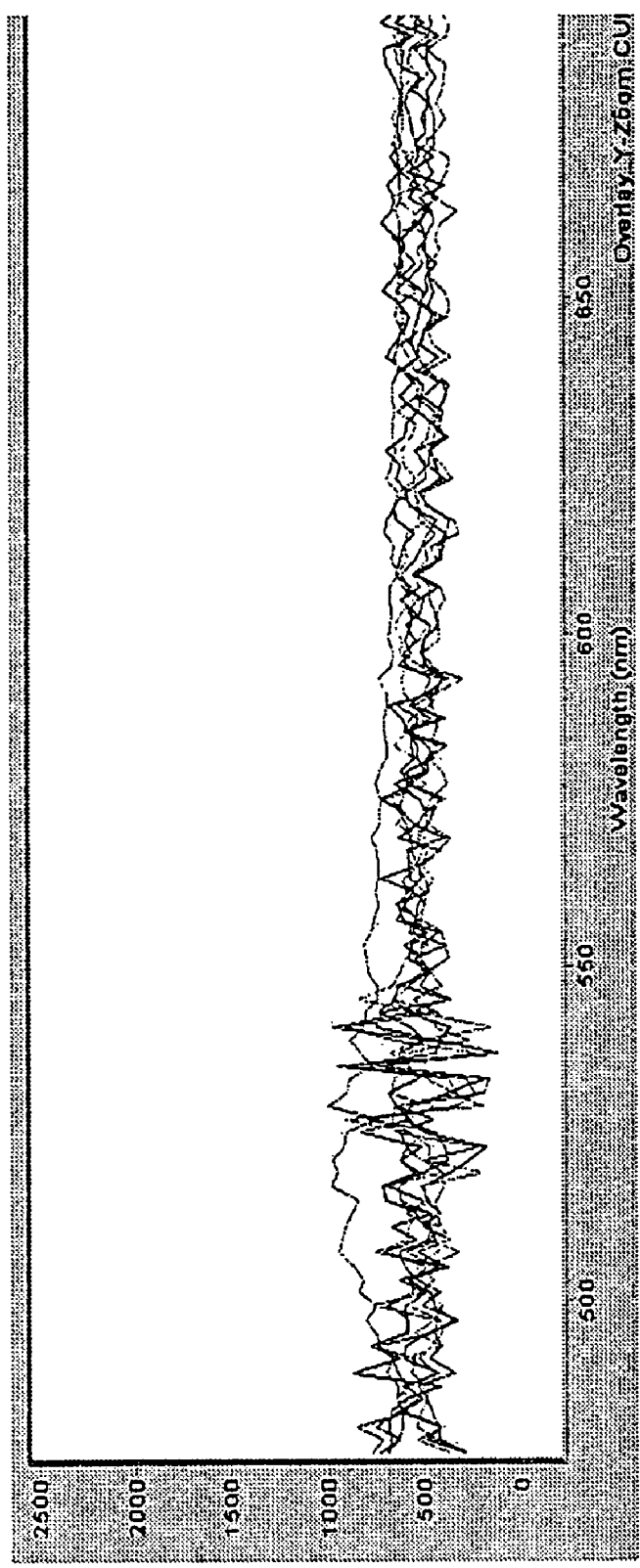
FIG. 5 shows the fluorescence spectra of a solution containing coated lenses comprising fluorescently labeled Con-A and Dextran as a function of time.

The rate of releasing of the Con A-rhodamine and the FITC-Dextran into a solution are measured by fluorescence spectroscopy. FIGS. 3 and 4 show that the Con A-rhodamine and the FITC-Dextran are slowly released into the solution from uncoated lenses over time in control experiments. FIG. 5 shows that Con A-rhodamine and the FITC-Dextran can be fully contained by the coatings.

A possible theoretical explanation for the results is that proposed by Decher et al. In a recent paper, Decher et al. demonstrated that a layer of montmorillonite can act as an effective barrier for metal cations. They proposed that the swelling and ion-induced bridging of the clay-platelets block or hinder ion-diffusion. The mechanism can be visualized like an over-lapping puzzle that locks in-place with other pieces. Almost nothing can penetrate through the resulting "wall" of clay puzzle-pieces.

The permeability of diffusive materials in the cores of contact lenses through layers of coating can be adjusted by changing the amount of clay and the native charge. It is conceivable that one could render the diffusive species captive with a very tight barrier layer.

In addition, one could use a relatively low molecular weight weak polyacid at a pH of from about 1.5 to about 8.5 with a low molecular weight weak polybase at a similar pH to produce a very "flat", dense bilayer coating. The density of the coating would be a function of pH and molecular weight. This type of coating system, without long polymeric side-chain, could also be used as a diffusion barrier like a clay layer.

What is claimed is:

1. A method for forming a diffusion-controllable coating on a medical device, comprising:
    applying at least one layer of clay onto the medical device to control the release of guest materials from the medical device, wherein the layer of clay consisting essentially of clay.

2. A method of claim 1, further comprising applying at least one layer of a first polyionic material.

3. A method of claim 2, wherein the clay is montmorillonite.

4. A method of claim 2, further comprising applying one or more layers of a second polyionic material.

5. A method of claim 4, wherein the medical device is an ophthalmic lens.

6. A method of claim 5, wherein the ophthalmic lens is a contact lens.

7. A method for manufacturing ophthalmic lenses without an extraction process, comprising:
    (1) producing ophthalmic lenses by molding in molds; and
    (2) forming a coating on each of the ophthalmic lenses produced in step (1) to control the release of guest materials from the ophthalmic lenses by:
        applying thereon one layer of clay, wherein the layer of clay consisting essentially of clay; and optionally applying a layer of a first polyionic material onto the ophthalmic lenses.

8. A method of claim 7, wherein said method comprises applying a layer of a second polyionic material.

9. A method of claim 8, wherein the clay is montmorillonite.

* * * * *